United States Patent [19]

Matsutani et al.

[11] Patent Number: 5,749,897
[45] Date of Patent: May 12, 1998

[54] SURGICAL NEEDLE AND MOLD FOR MANUFACTURING THE SAME

[75] Inventors: Kanji Matsutani; Motoichi Sugino; Hiroshi Yagisawa, all of Tochigi-ken, Japan

[73] Assignees: Kabushiki Kaisha; Matsutani Seisakusho, both of Tochigi-ken, Japan

[21] Appl. No.: 399,477

[22] Filed: Mar. 7, 1995

[30]    Foreign Application Priority Data

Aug. 23, 1994  [JP]  Japan ................................ 6-198333

[51]  Int. Cl.⁶ ............................................ A61B 17/00
[52]  U.S. Cl. ............................................ 606/222; 163/5
[58]  Field of Search ................................ 606/222, 223; 112/80.03; 223/102; 289/16; 163/5

[56]    References Cited

U.S. PATENT DOCUMENTS

| | | | |
|---|---|---|---|
| 3,038,475 | 6/1962 | Orcutt | 606/223 |
| 4,932,962 | 6/1990 | Yoon et al. | |
| 5,155,943 | 10/1992 | Matsutani et al. | 606/223 |

FOREIGN PATENT DOCUMENTS

| | | |
|---|---|---|
| 437329 | 7/1991 | Japan . |
| 453132 | 10/1991 | Japan . |
| 619983 | 10/1994 | Japan . |

OTHER PUBLICATIONS

Patent Abstracts of Japan, vol. 6, No. 263(M–181) Dec. 22, 1982 and JP–A–57 156140, Sep. 27, 1982.

Patent Abstracts of Japan, vol. 14, No. 367 (M–1008), Aug. 9, 1990 and JP–A–02 133137, May 11, 1990.

*Primary Examiner*—Jeffrey A. Schmidt
*Attorney, Agent, or Firm*—Townsend&Banta

[57]    ABSTRACT

A surgical needle has a top edge formed by two pressed faces located inside or outside of curvature from pressing a material blank made of austenitic stainless steel having fibrous texture and cutting edges formed on both sides of a base. The top edge is sharp at a needle point and the sharp needle point is constituted of fibrous texture formed at the surface layer of the material blank. Grinding marks extending crosswise formed on the face of the mold are transferred to the pressed faces. A mold constitutes plural faces forming projecting angles (angle between two intersecting faces is 180° or below, and the line at which the two faces intersect is made as a projecting line) along edges of the blocks made of two rectangular prisms, and constitutes a cavity by suitably contacting the edges of the blocks.

2 Claims, 4 Drawing Sheets

SURGICAL NEEDLE AND MOLD FOR MANUFACTURING THE SAME

CROSS-REFERENCE TO RELATED APPLICATION

This application claims priority benefits under 35 U.S.C §119 of Japanese application Serial No. 6-198,333, filed Aug. 23rd, 1994, the entire disclosure of which is incorporated herein by reference.

BACKGROUND OF THE INVENTION

1. Field of the Invention

This invention relates to a surgical needle for suture having a point of a triangle cross section and a mold for manufacturing the surgical needle.

2. Description of Related Art

A surgical needle for suture whose point has a triangular cross section, has keen cutting edges of certain length from the point, on both sides of the base of the triangular cross section and at a top edge opposing to the base. The surgical needle has a sharp needle point at which the respective cutting edges are integrated. The major part of the top edge is however formed in a gently curving shape without forming such a cutting edge. When an incised portion is to be sutured, the needle penetrates human's body tissues by its sharp needle point and incises them by the cutting edges, thereby passing through the tissues as pushing the incised tissues aside by the top edge. Such a triangular needle takes one of various thicknesses, arranges the top edge at either inside or outside, and is formed to be curving with predetermined curvature. A properly selected triangular needle is used according to the portions to be sutured. The inventors of this invention have previously proposed a method for manufacturing a triangular needle, as disclosed in Japanese Patent Publication No. 1-26,785, in which an intermediate material is made so that its distal end is formed in a triangular prism shape by pressing the original material and in which only base face opposing to the top edge of the intermediate material is ground. With this method, as shown in FIGS. 5A and 5B, a top edge 52 of the triangular prism 51 is molded into a blunt shape by pressing. Thus, grinding of oblique faces 55 located on both sides of the edge 52 is required to form a sharp needle point 54 in addition to grinding of the base face 53 of the prism 51.

The size of the original material for surgical needle is extremely fine as of 0.1 mm through 1.5 mm. A small cavity is formed in a mold for forming an intermediate material by pressing it. That is, such a small cavity is formed in a V-shape corresponding to the cross section of the surgical needle at the mold. The angle portion of the V-shaped cavity corresponds to the edge of the triangular prism. If such a V-shaped cavity would have been formed by a single material, it is impossible to fabricate the bottom of the cavity corresponding to the angle portion. For example, even if the material is cut or ground by a milling cutter or hone having a keen edge formed in association with the designated angle, it is impossible to form a V-shaped cavity having an accurate edge due to wearing of the cutter or hone as proceeding fabrications.

To solve this problem, a mold as disclosed in Japanese Unexamined Patent Publication No. 2-133,137 has been used for fabricating the original material. With the technique of the invention above, in order to mold a triangular prism corresponding to the cross section of the predetermined surgical needle, two quadratic prisms are ground off at their corners so as to respectively form a half of the triangular prism, or a triangle when viewed to its cross section, divided by a perpendicular drawn from the top edge to the base.

The mold can be formed by contacting those quadratic prisms with each other and allows the angle portion of the V-shape which makes the bottom of the cavity to be fabricated accurately.

Stainless steel is used as a material for such surgical needle. The surgical needle requires to have proper strength and stiffness because it will be subject to stress of complex directions when penetrating through the tissues. Therefore, martensitic stainless steel is ordinarily used. After formed with cutting edges and an eye and after curved into a predetermined shape, a surgical needle is given strength and stiffness by a heat treatment.

However, a problem arises which rust may occur if such martensitic stainless steel is not used for a long time of period after manufactured. To avoid this problem, this inventors have proposed and established a manufacturing technology of a surgical needle in use of austenitic stainless steel, as disclosed in Japanese Patent Publication No. 1-11, 084. In this technology, a wire rod made of austenitic stainless steel is wiredrawn with face reduction rate of 80% or above, and the drawn wire is fabricated while maintained at 500° C. or below to manufacture the surgical needle. That is, by cold wiredrawing of the wire rod of austenitic stainless steel, the needle gains rigidity and fiber-like, or fibrously, extended texture, and where the texture is maintained at the temperature of recrystallization or below, the surgical needle to be manufactured assures its strength and stiffness.

We found, as a result of proceeding of further research and development for surgical needle and its manufacturing technology, that the material cold wiredrawn from an austenitic stainless steel wire rod has the stiffest layer at its surface and reduces its stiffness as approaches the material center and that it would be advantageous to manufacture the surgical needle where such a surface layer is left on the needle.

However, the mold is for molding a triangular prism as an intermediate material by pressing the original material, so that when a sharp needle point is formed, two faces between the bottom and the edge are necessary to be ground. Hence, the needle point of the obtained surgical needle tends to be formed by grinding off the stiff surface layer.

SUMMARY OF THE INVENTION

It is an object of the invention to provide a mold capable of forming a sharp needle point with the hardest surface layer of the material therefor.

A mold according to the invention is constituted of a pair of rectangularly shaped blocks having oblique faces extending in a longitudinal direction of an edge of each block so that the oblique faces form a cavity for surgical needles when the blocks are contacted with each other so as to meet the opposing oblique faces to each other. The oblique face is formed of plural subdivided faces constituting an angle between them equal to 180° or below.

With the mold, when the blocks are contacted with each other, the cavity is formed of a cross-sectionally V-shaped groove having a larger cross section on a side of a needle proximal end than the cross section of the material blank and a smaller cross section on a side of a needle distal end than the cross section of the material blank and sharply intersecting edges at a V-shaped point. Therefore, when a material blank is inserted into the cavity and is then pressed, an intermediate material can be fabricated to be blunt on the side of the needle proximal end and keen on the side of the needle distal end.

The shape of the intermediate material is a transformed triangular pyramid whose top edge comes close to the base as approaches the needle distal end. Therefore, a surgical needle with a sharp point can be manufactured by grinding the intermediate material so as to make the base slightly close to the top edge. The needle point is substantially constituted of two faces located on both side of the top edge, and is constituted of the hardest surface layer of the material, which constitutes the two faces. Accordingly, almost the entire surface including the needle point is made of the surface layer of the material, so that surgical needles can be manufactured whose strength and stiffness are so maintained under the best condition.

A surgical needle according to the invention is made from austenitic stainless steel blank having fibrous texture, and has a top edge located inside or outside of curvature and made by two pressing faces, and cutting edges formed at both sides of inside or outside face of the curvature. The top edge becomes sharp on the needle distal end of the surgical needle, and a keen needle tip is constituted by the fibrous texture formed at the surface layer of material.

Such a surgical needle can maintain its strength and stiffness because the needle becomes sharper, or namely, changes from face contact to liner contact against the body tissues, as the top edge approaches the needle tip and because the sharp needle point is constituted of the hardest material's surface layer.

According to an embodiment of the invention, a surgical needle has a top edge located inside or outside of curvature and made by two pressed faces, cutting edges formed at both sides of inside or outside face of the curvature. A part of the pressed face is transferred with grinding marks extending in a cross direction formed on the oblique face.

With such a surgical needle, grinding marks in the cross direction are transferred from the oblique faces of the mold to at least a portion of the two pressed faces located on both sides of the top edge, and the serrate cutting edges can be made by the grinding marks, thereby reducing penetration resistance when the tissues are incised.

BRIEF DESCRIPTION OF THE DRAWINGS

The above and other objects and features of the invention are apparent to those skilled in the art from the following preferred embodiments thereof when considered in conjunction with the accompanied drawings, in which.

DETAILED DESCRIPTION OF THE PREFERRED EMBODIMENTS

Figure 1:
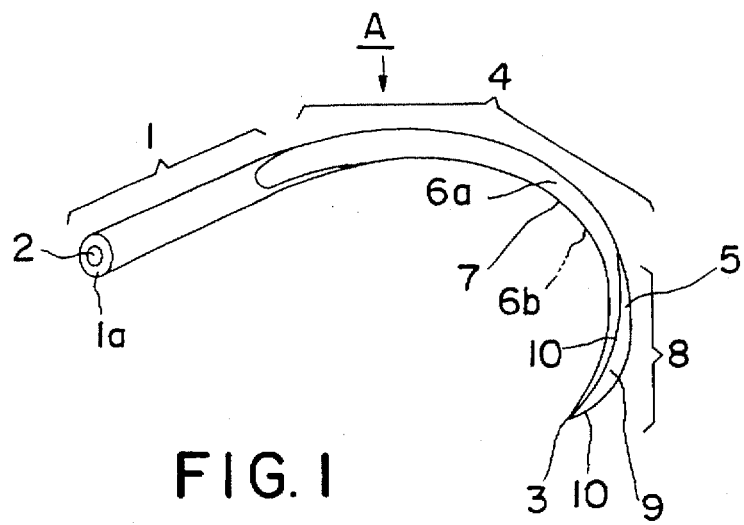
FIG. 1 is a perspective view showing a surgical needle according to the invention.

Referring to the drawings in detail, a surgical needle, as well as a mold for manufacturing it, according to a preferred embodiment of the invention is shown.

First, referring to FIGS. 1, and 2A–2D, constitution of a surgical needle A is described. The surgical needle A uses a material whose texture is made to be fibrously extended by cold wiredrawing of liner austenitic stainless steel material at a predetermined face reduction rate and which is fabricated to have a diameter equivalent to the diameter of the objective surgical needle A, and is manufactured using material blanks in which the material is cut at the length corresponding to the length of the objective surgical needle A. The material blank has fibrously extended texture from the center to the surface layer, and the hardness at the surface layer is harder than that at the center. The surgical needle A is therefore manufactured using the surface layer of the material blank as much as possible as the surface of the surgical needle A.

In FIG. 1, a hole 2 as means for connecting a suture is formed at an end 1a on the proximal end 1 as one end of the surgical needle A, and a sharp needle point 3 is formed at the other end. Cross sections between a needle body 4 and the needle point 3 are formed in a triangle made of a base 5, and oblique faces 6a, 6b, and a top edge 7 is formed corresponding to the top of the triangle.

The numeral 8 is a portion on a side of the distal end between the needle point 3 and the needle body 4; the needle tip portion 8 has predetermined length and is constituted corresponding to a ground face 9 which is ground so as to make the base 5 come close to the top edge 7 as approaches the needle point 3. Cutting edges 10 are formed on both sides of the ground face 9.

The top edge 7 is formed by the top of the oblique faces 6a, 6b formed by the mold B; the top edge 7 is made blunt on the side of the proximal end and keen on the side of the distal end, or namely changes from a blunt state to a keen state, as approaches to the needle point 3.

Figure 2A:
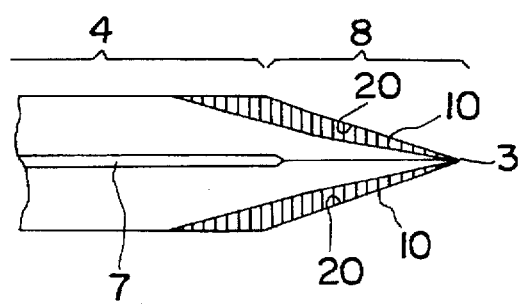
FIG. 2A is an enlarged top view of the surgical needle point of the surgical needle shown in FIG. 1.
Figure 2B:
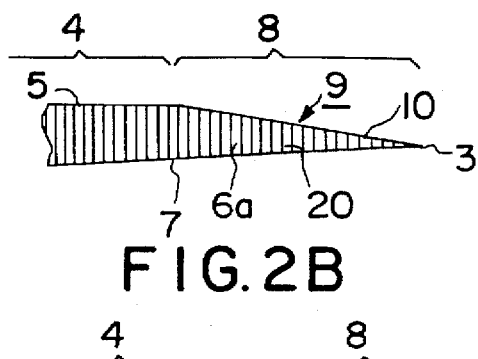
FIG. 2B is an enlarged side view of the needle point of the surgical needle shown in FIG. 1;.
Figure 2D:
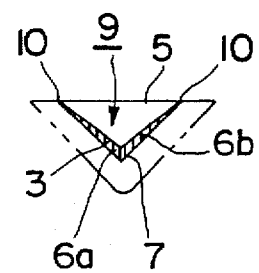
FIG. 2D is an enlarged front view of the needle point of the surgical needle shown in FIG. 1.
Figure 2C:
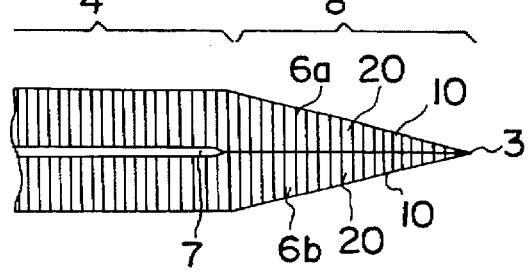
FIG. 2C is an enlarged top view of the needle point of the surgical needle shown in FIG. 1, showing the oblique faces.

That is, the needle tip portion 8 of the surgical needle A has the two oblique faces 6a, 6b, as shown in FIG. 2C formed by press and the ground face 9, is formed with the top edge 7 made from the oblique faces 6a, 6b to have sharpness so as to function as almost a cutting edge, and is formed with the cutting edges 10 made from the oblique faces 6a, 6b and the ground face 9 on both side of the ground face 9. The needle point 3 is formed at a point at which the cutting edges 10 and the top edge 7 are integrated.

Therefore, only the base 5 is ground when the needle point 3 is formed. The oblique faces 6a, 6b are not ground, at which the surface layer of the blank is left as it is. Accordingly, two faces at the needle tip portion 8 and three faces at the needle body 4 have the surface layer of the material blank in the surgical needle A, so that the surgical needle can maintain high strength and stiffness.

The surgical needle A thus constituted by remaining the surface layer of the material blank as much as possible, can oppose to large penetration resistance and large bending force occurring when passing through body tissues.

It is to be noted that although in this embodiment the surgical needle is formed as an eyeless needle by forming the hole 2 for connecting a suture at the end 1a, connecting means for a suture is not limited to such a structure, and the surgical needle can be as a matter of course formed as so called an eyed needle with a hole having elasity at the end 1a. The ground face 9 is not necessary to mean a face formed by grinding in use of a hone, and includes a face formed by removing the base 5 by a metal removing method, for example, such as, an electroerosion machining method when the cutting edges 10 are formed.

Figure 3A:
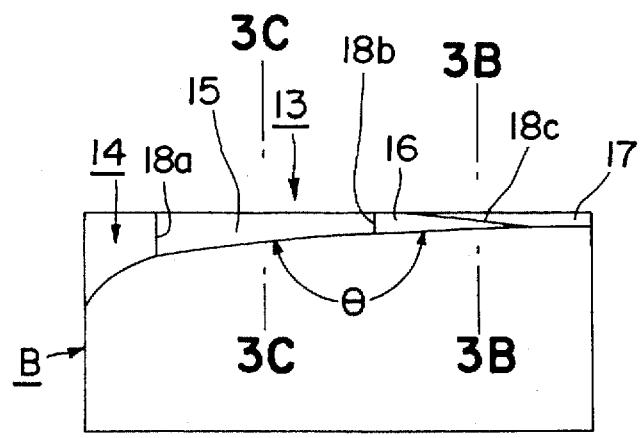
FIG. 3A is a perspective view of one block of the mold B for forming the surgical needle.
Figure 3B:
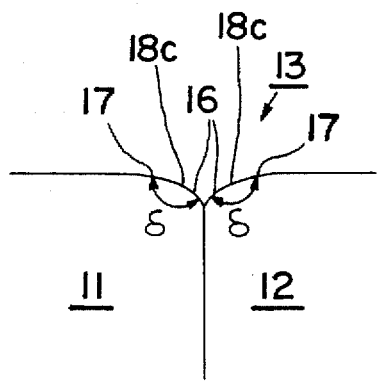
FIG. 3B is an enlarged rear view of the mold B for forming the surgical needle.
Figure 3C:
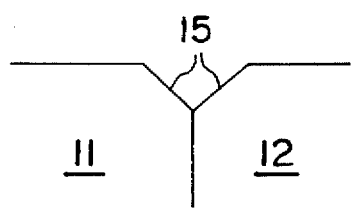
FIG. 3C is an enlarged front view of the mold B for forming the surgical needle.

Referring to FIGS. 3A–3C, constitution of a mold B for forming the surgical needle A is described. In FIGS. 3B–3C, the mold B is constituted of blocks 11, 12 made of two rectangularly shaped prisms. A half of the cross section of a cavity 13 and a leaking portion 14 in continuation with the cavity 13 are symmetrically formed at the corresponding edges of the blocks 11, 12, respectively, and the mold B is constituted by facing the blocks 11, 12 with each other and fixing them by means of fixing jigs or whatever not shown so as to oppose molding force.

The cavity 13 is formed of plural subdivided faces 15 to 17 having relationship of a projecting angle (the angle between two intersecting faces is 180° or below, and the line at which the two faces intersect is made as a projecting line) formed in correspondence with the needle body 4 and the needle tip portion 8 and is formed to have a V-shape with various depths in accordance with positions.

The cavity 13, when the material blank is pressed, is constituted to make the top edge 7 blunt at a portion corresponding to the needle body 4 and keen at a portion corresponding to the needle point 3, and is constituted so that the top edge 7 is surely formed to be sharp in accordance with the cross section of the cavity 13 in particular by rendering the cross section of the cavity smaller than the cross section of the material blank at a portion corresponding to the needle tip portion 8.

That is, the face 15 constituting the cavity 13 is formed in continuation with the leaking portion 14 formed at one end of the mold B, and is constituted as an area for forming the needle body 4. The face 15 has the same length as the needle body 4 of the surgical needle A, has depth that the cross section at a connection 18a between the face 15 and the leaking portion 14 is larger than the cross section of the material blank, and is formed in a V-shape having depth that the cross section at a position (connection 18b between the face 16 and the face 15) remotest from the leaking portion 14 is almost equal to or slightly larger than the cross section of the material blank.

The faces 16, 17 are constituted as areas for forming the needle tip portion 8, and are formed as to have sufficiently longer length than the length of the needle tip portion 8. The face 16 is formed in continuation with the face 15, and the connection 18b between the face 16 and the face 15 forms the projecting angle to form a V-shape that becomes shallower as remote from the connection 18b.

The face 17 is formed in a condition that it stacked against the face 16 with the projecting angle. Changes of depth of the face 17 with respect to the axis direction of the mold B are not restricted. In this embodiment, the face 17 is formed to be deeper as remote from the connection 18b. Therefore, the connection 18c between the faces 16, 17 forms a projecting angle thereat.

The cavity 13 composed of faces 15 to 17 described above can be formed without interference of the grinding machine with the already processed face at a time that subsequently processed face is to be ground where the edges of blocks 11, 12 are ground at their faces by a machine such as a plain grinder. For example, when plural faces are connected with an angle equal to or greater than 180° between the faces, whatever grinding order of the respective faces would interfere with the already processed area by the grinding tool, and it is impossible to form a suitable cavity.

Figure 4A:
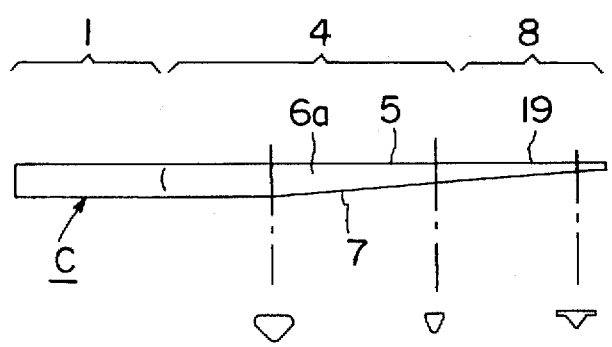
FIG. 4(a) is a side view of an intermediate material formed by pressing the material blank with the mold.
Figure 4B:
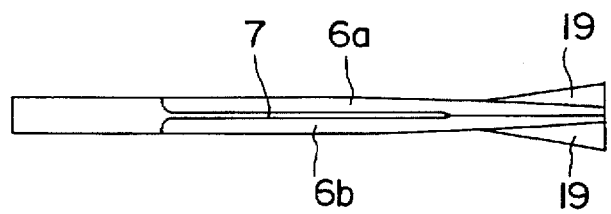
FIG. 4(b) is a top view of an intermediate material formed by pressing the material blank with the mold.
Figure 5A:
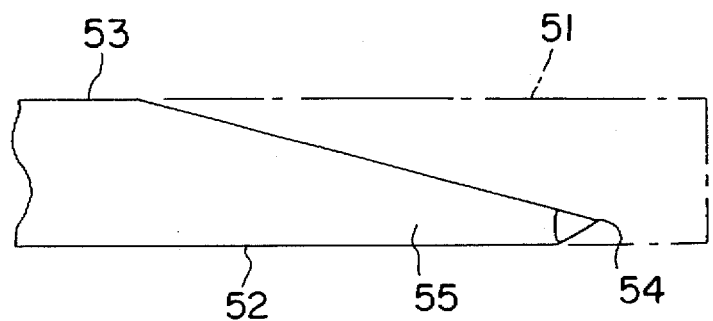
FIG. 5A is a side view partially cut away of a conventional surgical needle.
Figure 5B:
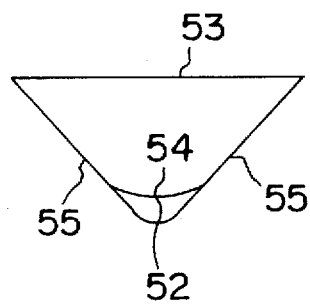
FIG. 5B is a front view of a conventional surgical needle.

Next, an intermediate material C manufactured by the mold B is described. The intermediate material C shown in FIGS. 4A and 4B is obtainable by pressing by the mold B a material blank (not shown) in which a liner material having diameter corresponding to the diameter of the objective surgical needle A is cut by a length corresponding to the length of the surgical needle A.

A portion corresponding to the needle body 4 of the intermediate material C is formed in a triangle with rounded corners because the cross section near the end 1 formed by opposing faces 15 is larger than the cross section of the material blank. At the needle point 3 and its vicinity, the top edge 7 is made relatively keen even though not functioning as a cutting edge.

At a portion corresponding to a needle tip portion 8 of the intermediate material C, the top edge 7 is made relatively keen and so do the edges on both sides of the base 5, because the cross section formed by the opposing faces 16 at the connection 18b between the face 15 and the face 16 is nearly equal to that of the material blank. The top edge 7 is made considerably keen even though not functioning as a cutting edge because the cross section formed by the opposing faces 16, 17 becomes smaller than that of the material blank as becoming remote from the connection 18b, and residual materials are formed on both sides of the base 5 as burrs 19.

A straight needle as a condition prior to bending process of surgical needle A shown in FIG. 1 can be manufactured by removing the burrs 19 at the needle tip portion 8 by grinding the base 5 of the intermediate material C, grinding the base 5 in accordance with the length of the predetermined needle tip portion 8 and with depth from the base 5 of the top edge 7 corresponding to that length to make the base 5 close to the top edge 7, and integrating the ground face 9 at which the base 5 is ground and two oblique faces 6a, 6b to form the needle point 3.

It is to be noted that although with the mold B the top edge 7 corresponding to the needle tip portion 8 is entirely made keen, it can be constituted that only a portion corresponding to the needle point 3 is made keen.

With surgical needles having cutting edges, it has been known that their incision characteristics can be improved by grinding, when the cutting edge is formed, in a direction intersecting the cutting edge, or preferably, in a perpendicular direction to the edge, and forming tiny serrate portions on the cutting edge. Therefore, serrate portions may be formed on the cutting edge by grinding the base opposing to the top edge and the two oblique faces, respectively, in a triangular needle. However, if the oblique faces are thus ground off, the process that the surface layer of the material blank is left becomes meaningless.

With the mold B according to the invention, the edges of the blocks 11, 12 corresponding to the faces 16, 17 are ground in a direction perpendicular to the axis direction of the material blank (a direction perpendicular to the top face of the mold B in FIG. 3B) by a plain grinder, and the faces 16, 17 remaining grinding marks (cross marks) formed at the edges are formed.

By molding the material blank using the mold B, the grinding marks 20 on the faces 16, 17 are transferred to the oblique faces 6a, 6b of the surgical needle A, and the serrate portions can be formed on the cutting edges 10 with the grinding marks and the ground face 9. That is, the grinding marks extending in the cross direction of the face can be formed without grinding the oblique faces 6a, 6b made of the surface layer of the material blank. Particularly, by grinding only the face 17 of the mold B to form the crosswise marks, the marks can be transferred to only the vicinity of the cutting edges 10 as shown in FIGS. 2A–2D.

As described above, with the mold according to the invention, the cavity is made by the subdivided faces having a relationship that the angle between the faces is 180° or below so as to project the connecting line between the faces, so that notwithstanding of processing order a predetermined cavity can be formed using a machine such as a plain grinder. Therefore, the mold can be easily manufactured with high accuracy.

With the surgical needle according to the invention, since the top edge approaching the needle point is formed to be keen by pressing the liner material made of austenitic stainless steel having fibrous texture, and since the sharp needle point is, by grinding the base opposing to the top edge, formed with the two faces sandwiching the top edge, the surgical needle can be constituted of the hard surface layer of the material blank, thereby maintaining the strength and stiffness of the material.

With the surgical needle according to the invention, since the top edge approaching the needle point is formed to be keen by pressing the material blank, since the sharp needle point is, by grinding the base opposing to the top edge, formed with the two faces sandwiching the top edge, and since grinding marks of the mold are transferred to the oblique faces, the surgical needle can be constituted of the hard surface layer of the material blank and the cutting edges with serrate portions can be constituted, so that the surgical needle can maintain the strength and stiffness of the material and reduce penetration resistance.

It is understood that although the present invention has been described in detail with respect to preferred embodiments thereof, various other embodiments and variations are possible to those skilled in the art which fall within the scope and spirit of the invention, and such other embodiments and variations are intended to be covered by the following claims.

What is claimed is:

1. A method of producing a surgical needle with a substantially triangular cross section comprising the steps of;

extending austenitic stainless steel by wiredrawing to make a material blank having fibrous texture at its surface;

forming a needle material blank with a substantially triangular cross section by pressing said material blank using a mold formed with a pair of blocks which have oblique faces to form a cavity so as to make a projecting angle between them less than 180°; and forming a pair of cutting edges on both sides of another face of said needle material opposing an edge which is formed between two pressed faces formed by said oblique faces of said mold by removing surface of said another face.

2. A method of producing a surgical needle according to claim 1, wherein ground marks extending crosswise to a longitudinal direction of said needle material blank is formed on said oblique faces of said mold so as to transfer fibrous texture onto said pressed faces of said needle material blank when said pressed faces are pressed.

* * * * *